(12) United States Patent
McNary et al.

(10) Patent No.: US 6,579,254 B1
(45) Date of Patent: Jun. 17, 2003

(54) MEDICATION ADAPTER AND METHOD FOR USE THEREOF

(75) Inventors: Richard McNary, Vernon, VT (US); Lawrence P. Hudon, Hinsdale, NH (US); Louis Woo, Arlington, VA (US)

(73) Assignee: Portex, Inc., Keene, NH (US)

( * ) Notice: Subject to any disclaimer, the term of this patent is extended or adjusted under 35 U.S.C. 154(b) by 158 days.

(21) Appl. No.: 09/597,775

(22) Filed: Jun. 19, 2000

(51) Int. Cl.[7] ............................................. A61M 1/00
(52) U.S. Cl. ................. 604/27; 604/158; 604/167.01; 604/109; 604/175; 604/174; 604/910; 128/203.12; 128/207.15; 128/207.16; 128/912; 606/109
(58) Field of Search ........................ 604/167.01, 158, 604/174, 175, 910, 27; 128/203.12, 207.15, 207.16, 912, 205.24, 202.27; 606/109

(56) References Cited

U.S. PATENT DOCUMENTS

| | | | |
|---|---|---|---|
| 3,739,778 A | * 6/1973 | Monestere et al. | 604/167.01 |
| 4,240,417 A | * 12/1980 | Holever | 128/203.12 |
| 4,416,273 A | * 11/1983 | Grimes | 128/207.16 |
| 4,552,142 A | * 11/1985 | Hoffman et al. | 128/207.16 |
| 4,598,707 A | * 7/1986 | Agdanowski et al. | 128/207.15 |
| 4,838,255 A | * 6/1989 | Lambert | 128/202.16 |
| 5,073,166 A | * 12/1991 | Parks et al. | 604/105 |
| 5,158,569 A | * 10/1992 | Strickland et al. | 604/533 |
| 5,501,596 A | * 3/1996 | Bailey | 433/86 |
| 6,154,897 A | * 12/2000 | Paini | 137/218 |

FOREIGN PATENT DOCUMENTS

| | | | | |
|---|---|---|---|---|
| WO | WO 95/08356 | * | 3/1995 | 128/214.4 |

* cited by examiner

Primary Examiner—Thomas Denion
Assistant Examiner—Theresa Trieu
(74) Attorney, Agent, or Firm—Louis Woo

(57) ABSTRACT

By interposing an adapter between the endotracheal or tracheal tube inserted to a patient and the ventilation and suction systems that are connected to the endotracheal tube, a medication catheter could be inserted via an input port built into the adapter so as to enable a medical personnel to provide medicaments to a patient without having to disconnect either one of the systems connected to the endotracheal tube. The adapter is configured to have a securing mechanism that allows the medical personnel to secure the medication catheter in place. A one way valve fitted to the apertured arm that forms the input port of the adapter prevents any back flow of fluid from the input port. The medication catheter is manufactured with calibration markings, most likely equally spaced, and a radiopaque line along its length to enhance the maneuvering and the positioning thereof in the patient so that the distal tip of the medication catheter could be accurately positioned to the desired location of the patient's tracheal/bronchial tree. As a result, the medicament is accurately provided to the appropriate location where the need is the greatest.

10 Claims, 2 Drawing Sheets

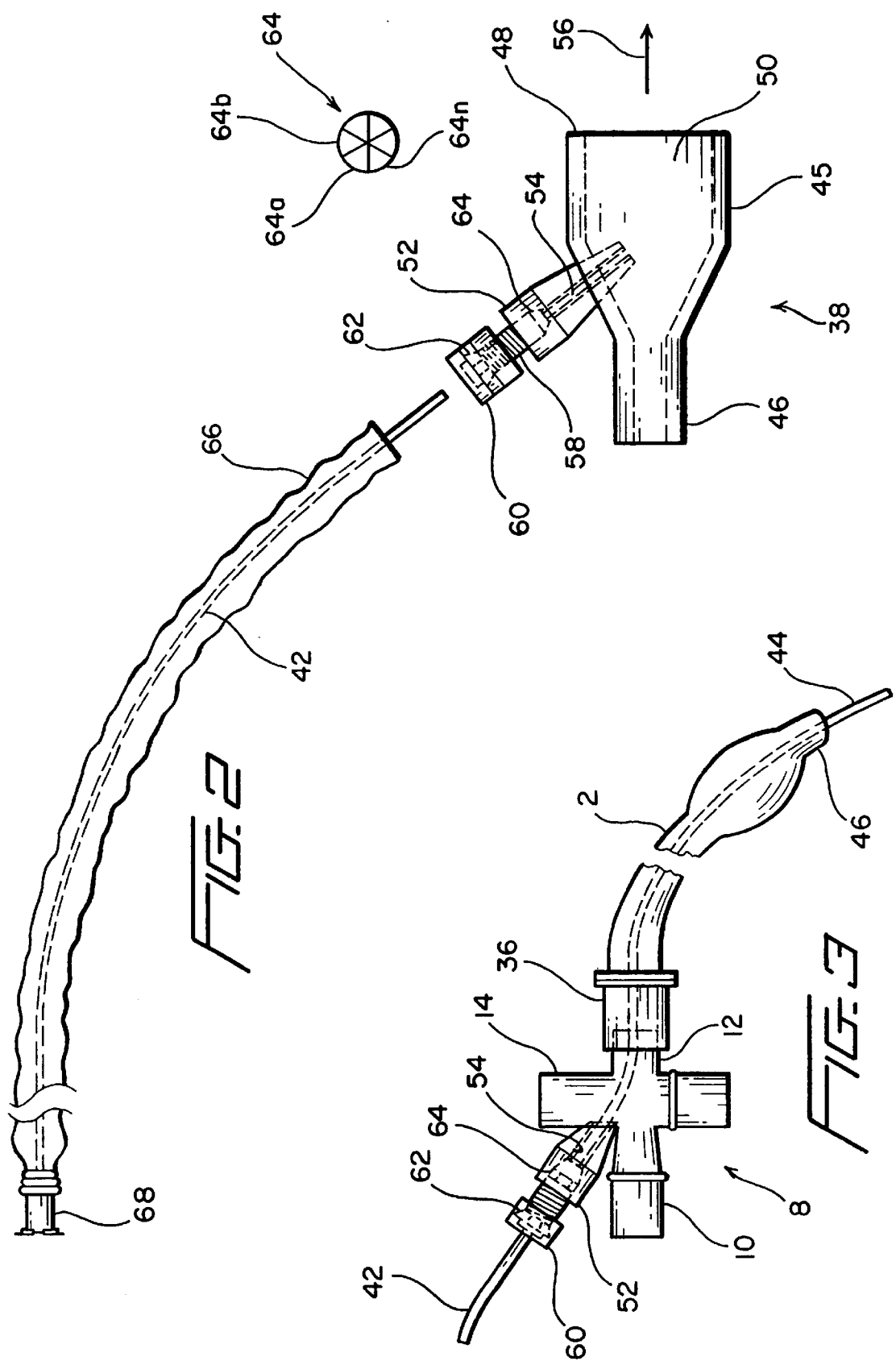

MEDICATION ADAPTER AND METHOD FOR USE THEREOF

FIELD OF THE INVENTION

The present invention relates to the supplying of a medication to a patient through either an endotracheal tube or a tracheal tube, and more specifically to the provisioning of an adapter to an endotracheal breathing circuit connected to the patient so that medication can be provided to the patient without having to disassemble the circuit.

BACKGROUND OF THE INVENTION

To enhance the breathing of a patient with a tracheal tube or an endotracheal tube, ventilation and suction systems are used. These systems are connected, by means of a connector, to the tracheal tube. (The term endotracheal tube henceforth should be taken to mean either an endotracheal tube or a tracheal tube.) The ventilation system provides ventilation to the patient while the suction system removes the fluids such as for example mucus secretions that accumulate in the trachea and the bronchi of the patient.

Oftentimes a patient connected to a tracheal tube has an acute lung injury. Consequently, medication must be provided to the patient. However, given that the endotracheal tube is connected in circuit with both the ventilator and the suction systems, prior to the instant invention, to supply medication to the patient, the systems, or at least one of the systems, connected to the patient's endotracheal tube has to be removed before medication may be supplied to the lungs of the patient. Needless to say, such removal and replacement of the ventilator and suction lines to the endotracheal tube is cumbersome, and oftentimes causes discomfort to the patient.

PCT publication WO95/08356 by the Assignee of the instant invention discloses the addition of an adapter in the ventilation circuit of the patient. The complete disclosure of the '356 publication is incorporated by reference to the disclosure of the instant application. The instant invention is an improvement of the adapter disclosed in the '356 publication. An alternative embodiment, as well as a method of using the same are also disclosed herein.

BRIEF DESCRIPTION OF THE PRESENT INVENTION

To ensure that a patient having endotracheal tube inserted to his trachea is continuously connected to the ventilator and the suction system while medication is being provided, an adapter is interposed between the ventilator and the endotracheal tube of the patient. An input port is provided to the adapter so that a catheter that has calibration markings thereon and preferably a radiopaque line extending along its length is insertable to the adapter via the input port. To prevent back flow of fluids from the patient, fitted within the input port is a one way valve that opens only when the catheter is pressed thereagainst and subsequently passes therethrough. The input port, in conjunction with the adapter, would guide the catheter along the length of the endotracheal tube. The catheter is movable therealong until the distal end of the catheter extends beyond the distal end of the endotracheal tube.

With the aid of the equally spaced calibration markings and the radiopaque line along the catheter, the catheter may be accurately positioned to a desired location in the lungs of the patient. Once thus positioned, a medicament may be provided to the proximal end of the catheter, and be guided by the catheter to the desired location in the patient.

To regulate the length of the catheter inserted to the patient, a securing mechanism in the form of an internally threaded collar with extending fingers fitted thereto is threaded over the input port of the adapter, which in turn has at its upper arm an externally threaded portion that threadingly mates with the internal threads of the collar. When the collar is turned tightly on the arm of the input port, the fingers at the collar would compressively grasp the catheter, to thereby retain the catheter in place so that its distal end remains accurately positioned with respect to the desired location of the patient where the medication is to be supplied.

An alternative embodiment of the instant invention encompasses the incorporation of the adapter to the connector piece that acts as a junction for communicatively connecting the ventilator, the suction system and the endotracheal tube.

It is therefore an objective of the present invention to provide an adapter that allows medication to be provided to a patient fitted with an endotracheal tube without having to disassemble the ventilator and/or the suction system that are connected to the endotracheal tube.

It is another objective of the present invention to provide an improved adapter.

It is yet another objective of the present invention to incorporate an adapter to the main connector that jointedly connects the ventilator circuit, the suction circuit and the endotracheal tube.

BRIEF DESCRIPTION OF THE FIGURES

The above-mentioned objectives and advantages of the present invention will become apparent and the invention itself will best be understood with reference to the following description taken in conjunction with the accompanying drawings, wherein:

FIG. 2 is an illustration of the adapter of the instant invention, and its coaction and relationship with a medication catheter; and FIG. 3 is an illustration of an alternative embodiment of the adapter of the instant invention.

DETAILED DESCRIPTION OF THE PRESENT INVENTION

Figure 1:
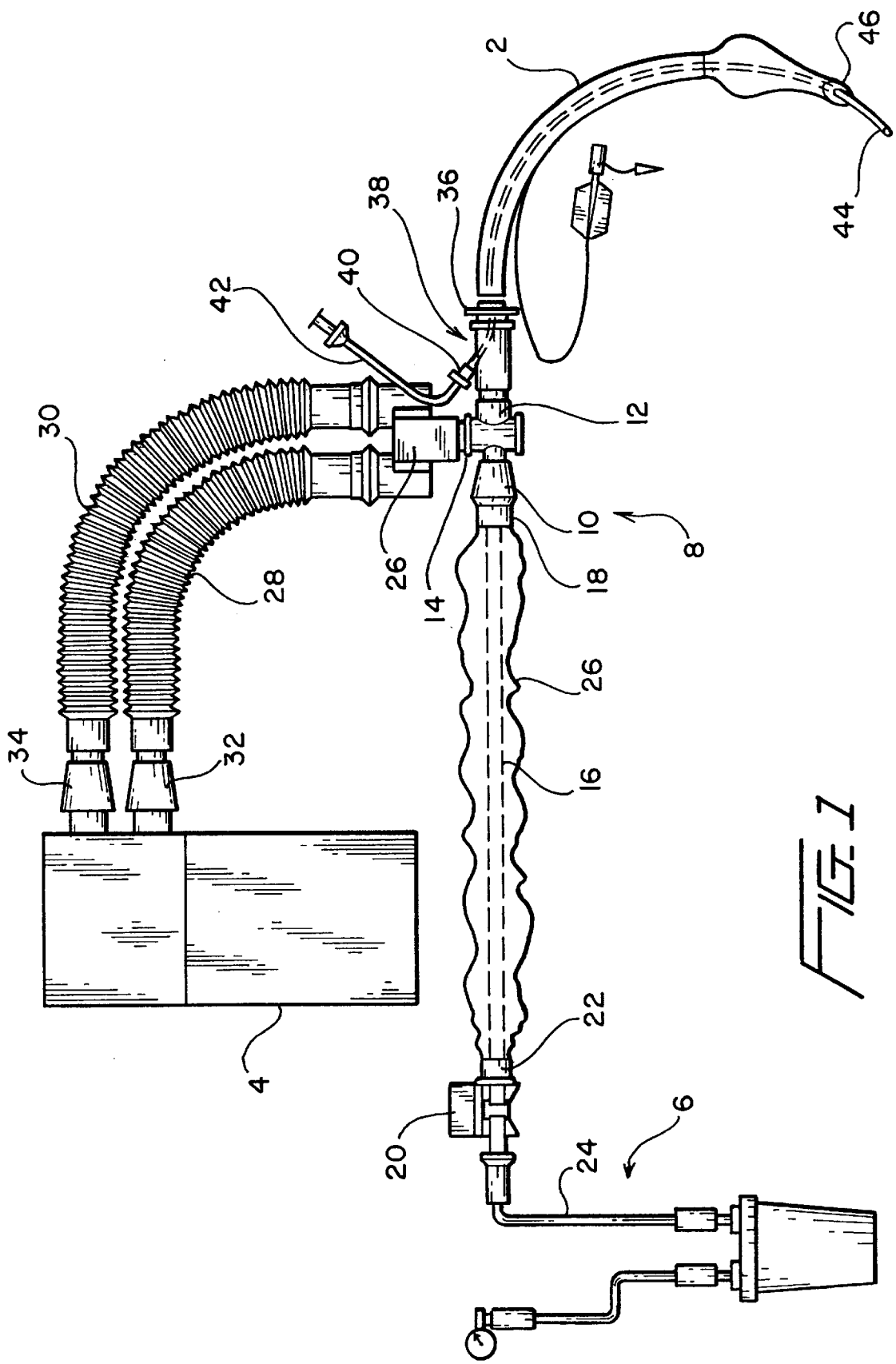
FIG. 1 is a schematic illustration of an overall view of the endotracheal tube being connected to a ventilator and a suction system, with the adapter of the instant invention being interposed between the endotracheal tube and the ventilator and suction system.

With reference to FIG. 1, an overall illustration of the interconnections of an endotracheal tube, a ventilator system, a suction system, and the instant invention adapter is shown. In particular, an endotracheal tube or a tracheal tube 2 is shown to be in communication with a ventilator 4 and a suction system 6. The communications among endotracheal tube 2, which is inserted into a patient (not shown for the sake of simplicity), ventilator 4 and suction system 6 are established by means of a junction connector 8. As shown, junction connector 8 is cross shaped and has a first leg 10, a second leg 12 and a third leg 14. Additional legs, not shown, may also be incorporated to connector 8.

Leg 10 is coupled to a suction catheter 16 by means of an appropriate coupler such as 18. The other end of suction catheter 16 is connected to a control valve mechanism 20, by way of a coupler 22. Control valve mechanism 20 is connected to a vacuum line 24, that in turn is connected to a conventional vacuum source usually built into the wall of the room of the patient. Enclosing suction catheter 16 is a protective sleeve 26, which collapses when suction catheter 16 is inserted through endotracheal tube 2 to the trachea/bronchial tree of the patient for removing fluids collected thereat by way of suction.

Connected to leg 14 of junction connector 8 is a coupler 26 that is connected to the distal ends of two flexible conduits 28 and 30. The respective proximal ends of conduits 28 and 30 are connected, by corresponding couplers 32 and 34, to ventilator 4. The combination of conduits 28, 30 and ventilator 4 could be considered as a ventilator circuit that mechanically pumps and removes air to the patient. Such ventilator circuit for ventilating a patient is conventional.

Interposed between leg 12 of cross connector 8 and the proximal end 36 of endotracheal tube 2 is an aperture adapter 38 of the instant invention. As shown in FIG. 1, adapter 38 has an input port 40 that allows a medication catheter 42 to be inserted to endotracheal tube 2 so that its distal end 44 could be moved along the length of endotracheal tube 2 and eventually extended beyond tip 46 thereof. Medication catheter 42 can then be maneuvered to a desired location at the trachea/bronchial tree of the patient. Once positioned at the desired location, a medicament such as for example recombinant surfactant protein C (rSPC surfactant), also know as "venticute", could be supplied to that desired location of the trachea/bronchial tree of the patient.

To enhance its movement along the length of endotracheal tube 2 and inside the patient, medication catheter 42 has along its length calibrated markings that allow a user to readily gauge the length of the catheter that has been inserted to the patient. To further enhance the maneuvering of medication catheter 42, a radiopaque line is integrated along substantially its entire length.

FIG. 2 provides an enlarged view of adapter 38 of FIG. 1. In particular, adapter 38 has a main body 45 having a proximal end 46 that is matingly coupled to leg 12 of cross connector 8. Distal end 48 of adapter 38, on the other hand, is matingly coupled to connector 36 of endotracheal tube 2. Adapter 38 is hollow so that a fluid path 38 is created along its length to enable free passage of suction catheter 16, as well as bidirectional passage of air from the ventilator circuit.

At a side of body 38 there is fitted an apertured arm or extension 52. Apertured arm 52 thus provides an input port to adapter 38. Aperture 54 in arm 52 has a sufficient dimension to allow medication catheter 42 to pass therethrough. Arm 52 is incorporated or fitted to body 38 at an angle relative to the longitudinal axis of body 45, so as to enable catheter 42, once inserted to arm 52, to pass therealong and be routed along the direction as indicated by per directional arrow 56.

Arm 52 has a top portion 58 that is externally threaded. An internally threaded collar 60 is threadingly mated to portion 58 of arm 52. Collar 60 is moreover internally fitted with a number of fingers 62, better shown in FIG. 3, that are compressible toward each other when collar 60 is threaded onto portion 58. The relationship of fingers 62 with medication catheter 42 is such that once catheter 42 is inserted to arm 52, upon collar 60 being fully threaded onto portion 58, fingers 62 would compress in unison onto the outer surface of catheter 42, without occluding catheter 42, at the location where it makes contact with fingers 62, so that catheter 42 is grasped by fingers 62 and be fixedly retained in position.

Further fitted to arm 52 is a one way valve 64 such as for example a duck bill valve. As shown by its enlarged planar view, one way valve 64 has a number of pliable flaps or portions 64a–64n that have sufficient elasticity so as to open just enough to enable catheter 42 to pass therethrough, and yet nonetheless would prevent any fluid in path 50 from flowing backwards out of arm 52. Upon removal of catheter 42 from arm 52, pliable portions 64a–64n would return to their respective original positions to act as a stop to prevent any back flow of fluids from the patient. For the illustration in FIG. 2, pliable portions 64a–64n could be considered to be opened along the direction into the paper.

FIG. 3 is an alternative embodiment of the instant invention in which apertured arm 52 is integrated directly to cross connector 8. Arm 52 is integrated to connector 8 at an appropriate angle so that catheter 42 could easily be inserted into endotracheal tube 2. All components discussed above with reference to arm 52 in FIG. 2 are present in the embodiment shown in FIG. 3.

In operation, medication catheter 42, which is enveloped by a protective sleeve 66 as shown in FIG. 2, is inserted to apertured arm 52 by way of collar 60, which has an opening, not shown, that matches aperture 54 of arm 52. As the distal tip 44 of catheter 42 makes contact with the pliable fingers 64a–64n of fitting 64, it pushes the pliable fingers 64 in a direction toward connector 8 so that an opening is formed to enable catheter 42 to pass therethrough. By reading the calibrated markings along catheter 42, the length of catheter 42 that is being inserted to arm 52, and subsequently to endotracheal tube 2, is readily determined. And with the length of catheters 42 and the combined distances or lengths of arm 52, connector 8 or body 45 (the FIG. 2 adapter), and endotracheal tube 2 known, the user can readily determined when distal tip 44 of catheter 42 is extended beyond tip 46 of tracheostomy tube 2.

Further, with the radiopaque line incorporated along substantially its entire length, catheter 42 could be readily maneuvered to precisely position its distal tip 44 to the appropriate location in the lung of the patient. Thereafter, a medicament container such as for example a syringe is inserted to the input 68 at the proximal end of catheter 42. By pushing in the plunger of the syringe, the medicament such as for example the venticute as mentioned previously is squirt into catheter 42 and conveyed therealong to output, at distal tip 44, to the desired location in the lung of the patient. Thus, given that the medicament is applied to substantially the desired precise location, a smaller dose of the medicament would achieve the same result as the larger doses in the prior art. Moreover, the medicament is concentrated in the particular area of need and therefore would act more quickly as compared to the prior art methods of non-localized application of the medicament.

Inasmuch as the present invention is subject to many variations, modifications and changes in detail, it is intended that all matter described throughout this specification and shown in the accompanying drawings be interpreted as illustrative only and not in a limiting sense. Accordingly, it is intended that the invention be limited only by the spirit and scope of the hereto appended claims.

What is claimed is:

1. In combination, an endotracheal or tracheal tube having a distal end insertable to a patient, a connector for connecting a suction line to said tube, a suction catheter for carrying suction insertable through and removable from said tube, an input port integrated to said connector at an angle to the longitudinal axis of said connector, a one way valve positioned within said input port, a medication catheter for medicament delivery having a proximal end and a distal end insertable to said input port of said connector to open said one way valve, said medication catheter being guided by said input port to said tube when said suction catheter is not present in said tube so that its distal end is extendable through and beyond the distal end of said tube, the distal end of said medication catheter being movable to at least one selected location in the lungs of the patient, a medicament container matable with the proximal end of said medication catheter for supplying thereto the medicament stored therein, said medication catheter guiding the medicament to said one selected location of the lungs of the patient.

2. Combination of claim 1, wherein said connector comprises:

a cross connector to which said suction line and a ventilation line are communicatively coupled; and an adapter whereto said input port is integrated.

3. Combination of claim 2, wherein said input port of said adapter comprises an apertured arm having mounted at its proximal end a securing means for selectively preventing the movement of said medication catheter through said arm.

4. Combination of claim 3, wherein said one way valve comprises a fitting having a plurality of pliable portions that open just enough to allow said medication catheter to pass through when said medication catheter is inserted to said arm, said portions of said fitting returning to their respective at rest positions when said medication catheter is withdrawn from said arm to thereby prevent fluid back flow through said arm.

5. Combination of claim 3, wherein said securing means comprises:

threads formed at the outer surface at the proximal end of said arm;

an internally threaded collar matable with the threads at the proximal end of said arm; and fingers fitted to the inside of said collar compressible in response to the tightening of said collar on said arm, said fingers grasping said medication catheter and maintaining it in place when said collar is fully threaded to said arm.

6. Combination of claim 2, wherein said medication catheter has integrated along substantially the length thereof a radiopaque line and equally spaced markings for enhancing the placement of said medication catheter inside the patient.

7. Combination of claim 1, wherein said connector comprises a cross connector having communicatively integrated thereto said input port, said cross connector further communicatively connectable to said suction line and a ventilation line.

8. Combination of claim 1, wherein said input port comprises an apertured arm having mounted at its proximal end a securing means for selectively preventing the movement of said medication catheter through said arm.

9. Combination of claim 8, wherein said one way valve comprises a fitting having a plurality of pliable portions that open just enough to allow said medication catheter to pass through when said medication catheter is inserted to said arm, said portions of said fitting returning to their respective original positions when said medication catheter is withdrawn from said arm to thereby prevent fluid back flow through said arm.

10. In combination, an endotracheal or tracheal tube having a distal end insertable to a patient, connector means for connecting at least a suction line to said tube, an input port integrated to said connector means, a one way valve positioned within said input port, a catheter for medicament delivery having a proximal end and a distal end insertable to said input port of said connector means to open said one way valve, said catheter being guided by said input port to said tube so that its distal end is extendable through and beyond the distal end of said tube, the distal end of said catheter being movable to at least one selected location in the lungs of the patient, a medicament container matable with the proximal end of said catheter for supplying thereto the medicament stored therein, said catheter guiding the medicament to said one selected location of the lungs of the patient;

wherein said input port comprises an apertured arm having mounted at its proximal end a securing means for selectively preventing the movement of said catheter through said arm; and wherein said securing means comprises:

threads formed at the outer surface at the proximal end of said arm;

an internally threaded collar matable with the threads at the proximal end of said arm; and fingers fitted to the inside of said collar compressible in response to the tightening of said collar on said arm, said fingers grasping said catheter and maintaining it in place when said collar is fully threaded to said arm.

\* \* \* \* \*